(12) United States Patent
Heuer

(10) Patent No.: US 12,714,483 B2
(45) Date of Patent: Aug. 25, 2026

(54) BONE ANCHOR FOR OPTIMISED CEMENT APPLICATION

(71) Applicant: MIMEO MEDICAL GMBH, Filderstadt (DE)

(72) Inventor: Frank Heuer, Filderstadt (DE)

(73) Assignee: MIMEO MEDICAL GMBH, Filderstadt (DE)

( * ) Notice: Subject to any disclaimer, the term of this patent is extended or adjusted under 35 U.S.C. 154(b) by 618 days.

(21) Appl. No.: 18/007,839

(22) PCT Filed: Jun. 2, 2021

(86) PCT No.: PCT/EP2021/064855

§ 371 (c)(1),
(2) Date: Dec. 2, 2022

(87) PCT Pub. No.: WO2021/245169

PCT Pub. Date: Dec. 9, 2021

(65) Prior Publication Data

US 2023/0225776 A1 Jul. 20, 2023

(30) Foreign Application Priority Data

Jun. 3, 2020 (DE) ..................... 10 2020 003 320.2

(51) Int. Cl.
*A61B 17/86* (2006.01)
*A61B 17/88* (2006.01)

(52) U.S. Cl.
CPC ........ *A61B 17/864* (2013.01); *A61B 17/8811* (2013.01)

(58) Field of Classification Search
CPC .......................... A61B 17/864; A61B 17/8811
See application file for complete search history.

(56) References Cited

U.S. PATENT DOCUMENTS 8,357,201 B2 * 1/2013 Mayer ................ A61F 2/30749 623/18.11
9,827,028 B2 * 11/2017 Biedermann ...... A61B 17/8625
2013/0144344 A1 6/2013 Giancola
(Continued)

FOREIGN PATENT DOCUMENTS

DE 3508759 A1 10/1985
DE 102011112890 A1 7/2012
(Continued)

OTHER PUBLICATIONS

International Search Report and Written Opinion received for PCT/EP2021/064855, mailed Sep. 17, 2021.

*Primary Examiner* — Tracy L Kamikawa
(74) *Attorney, Agent, or Firm* — Greer, Burns & Crain, Ltd

(57) ABSTRACT

A bone anchor for the fixation of bone components and bone fragments, including a shaft, a neck area and a head located in proximal direction and a tip located in distal direction, wherein the bone anchor has a mainly cylindrically shaped hollow chamber extending along the central axis, wherein the hollow chamber is adjacent a transition zone located proximally from a central plane, the transition zone at least partially has an inner diameter and the hollow chamber at least partially has an opening diameter, and the opening diameter of the hollow chamber is greater than the inner diameter of the proximal transition zone.

17 Claims, 8 Drawing Sheets

(56) References Cited

U.S. PATENT DOCUMENTS

2014/0276347 A1* 9/2014 Stone .................. A61M 27/002
604/9
2017/0245851 A1 8/2017 Biedermann et al.

FOREIGN PATENT DOCUMENTS

DE 102011017602 A1 10/2012
EP 2140824 A1 1/2010
EP 3210554 A1 8/2017
WO WO-2020008309 A1 * 1/2020 ......... A61B 17/7032

* cited by examiner

BONE ANCHOR FOR OPTIMISED CEMENT APPLICATION

BACKGROUND

Osteoporosis is characterised by a decrease in the structural integrity of the bone. This often results in compression fractures that need to be treated surgically. Due to the reduced bone quality, the clinical challenge is the insufficient anchorage stability when treated with bone anchors.

DE3508759A1 discloses a bone screw for the treatment of femur fractures. The patent application describes a bone screw with a centrally arranged cannula opening and several openings running laterally, which serve to allow bone cement to be injected through the bone screw into the bone. After hardening of the bone cement, a significantly higher strength is achieved between the bone and the bone screw.

For bone anchors to be used minimally invasively, the cannula opening must pass completely through the bone anchor so that the bone anchor can be inserted into the bone guided by a guide wire. If cementable bone anchors with a through hole are used, however, there is a risk that bone cement can spread outside the bone during bicortical screw fixation, which can cause serious complications.

From EP2140824A1, bone anchors are known that are optimised for bone cement restoration in such a way that they can be closed distally with a plug after minimally invasive insertion into the bone to prevent cement leakage. However, the disadvantage is that such a mini-plug must be kept in stock as an extra component and the handling must provide sufficient safety against unintentional loss of the mini-plug. A one-piece construction without moving parts would therefore be desirable.

Furthermore, it is necessary that the user keeps the injection cannula in contact with the bone anchor until the cement has completely hardened. If the injection cannula is removed prematurely, the high application pressure may cause the bone cement to leak backwards out of the bone anchor. This can cause complications in the further course of the operation. No currently known bone anchor prevents the cement from leaking backwards when an application cannula is removed directly after injection. A corresponding solution would have the great advantage of a significantly faster application and a significant material saving with regard to the necessary injection cannulas. With the conventional cement augmentation procedure, for each bone anchor one injection cannula is necessary.

DETAILED DESCRIPTION

This is solved by the bone anchor (10) according to the invention, whereby bone anchors (10) are built up into a composite or osteosynthesis construct (1) of two or more bone anchors. The relevant prior art is available for this purpose, which is why it will not be discussed in detail here.

For the bone anchor (10) according to the invention, space-allocating coordinate references are defined, such as the proximal direction (101), the distal direction (102), which extend along a central axis (103). Extending outwards from the central axis (103), the radial dimension (104) is defined. The circumferential dimension (105) is defined by a constant radius and along a variable circumferential angle (FIG. 1). Furthermore, there is a central plane (106) which separates the distal (102) and proximal (10) directions from each other.

In a first embodiment, a bone anchor (10) for the fixation of bone components and bone fragments is described, which consists of a shaft (13), a neck area (12) and a head (11) located in proximal direction (10), as well as a tip (14) located in distal direction (102).

It should also be mentioned that the bone anchor (10) is optimally formed in one piece and manufactured using an additive process. If the bone anchor (10) cannot be manufactured using an additive process, a multi-part construction of the bone anchor is suitable, which is assembled using any method known in the prior art. The head (11) is preferably formed as a lens, an inclined head or a spherical head. However, a composition of different curves and surfaces is also possible. The main feature of the head is that the head (11) has a greater outer diameter than the neck area (12). Preferably, the bone anchor has a tool attachment point (19) which is suitable for introducing a torque. For minimally invasive treatment, it is advantageous that the bone anchor has a cannula opening (15, 16, 40, 20, 30) passing completely through it, through which a surgical guide wire can be passed.

Bone anchors are preferably bone screws that can be screwed to a bone. However, hooks, clamps, nails and other types of bone anchors can also be used. In the example of a bone anchor (10) shown here, a bone screw with a shaft (13) and a bone thread (131) located on the shaft is presented. The thread (131) may have a finer toothing (132) in sections, which is more suitable for a harder cortical bone. A tapered thread (132) with a cutting edge (133) at the bone anchor tip (14) is advantageous so that the bone anchor can self-tap into the bone when screwed in.

In the case of weak bone, such as osteopenia or osteoporosis, it may be necessary to augment the bone anchor additionally. This can be done with bone cement. Bone cement is preferably a polymer that is mixed from at least two components and injected in a liquid or paste-like state. The bone cement hardens after a few minutes in the bone to form a plastic and bonds with the sponge-like bone structure. A polymethyl methacrylate cement is usually used. Alternatively, other media for delivery through the bone anchor are conceivable. It is conceivable that alternative media, such as pharmaceutically active media, or media containing cells, nutrients, or media serving as hereditary information carriers, or vaccines are administered through the bone anchor. Therefore, throughout this document, the injectable medium is referred to simply as liquid (17).

Inside the bone anchor (10) there is a mainly cylindrically shaped hollow chamber (40) extending along the central axis (103) (FIG. 2), the hollow chamber (40) being adjacent to a transition zone (30) located proximally (101) from a central plane (106). This transition zone (30) has an inner diameter (d30) at least in sections and the hollow chamber (40) has an opening diameter (d40) at least in sections. The opening diameter of the hollow chamber (d40) is greater than the inner diameter (d30) of the proximal transition zone (30). This difference in cross-section (cf. d40 and d30) impedes a backflow of the liquid (17) when it is already in the hollow chamber (40).

The hollow chamber (40) is provided in distal-proximal alignment mainly centrally in the interior of the bone anchor (10). As described above, it is advantageous that the hollow chamber (40) is configured in such a way that it extends at least in sections with a constant opening diameter (d40) along the central axis (103) and that the hollow chamber (40) adjoins at least one transition zone (20, 30). Optionally, the hollow chamber (40) has at least one laterally extending opening (411, 412, 421, 422) communicating with the hollow chamber. Preferably, the openings are arranged in a circumferential ring-like formation (41 or 42). In the case of more than one circumferential ring-like opening formation (41 and 42), the openings have different opening diameters per formation. In bone anchors (10) screwed into bone, the lateral openings communicate with the surrounding bone tissue from the hollow chamber (40). They are configured so that the liquid (17) injected into the bone anchor (10) is delivered through the lateral openings into the surrounding tissue. A different diameter of the opening formations (41, 42) has the advantage that due to the local pressure difference within the liquid (17), a similar volume flow is generated through all openings (411, 412, 421, 422). This is achieved because the openings (421, 422, 42) closer to the proximal transition zone (30) have a smaller diameter than the openings (411, 412) of the formation (41) further distally.

In the further proximal course (101) along the central axis (103), i.e. after the proximal transition zone (30), there is an opening (16) which is suitable for receiving a cannula at least in sections (FIG. 2). The opening diameter (d16) of the opening (16) adjacent to the proximal transition zone (30) is greater than at least a portion of the inner diameter (d30) of the proximal transition zone (30). Furthermore, it is advantageous if the opening (16) opens into the tool attachment point (19) in proximal direction (101).

To reduce the risk of unintentional leakage of the liquid (17) distally (102), it is advantageous that the hollow chamber (40) is also adjacent to a transition zone (20) located distally (102) from a central plane (106), and the distal transition zone (20) has, at least in sections, an inner diameter (d20) and the hollow chamber (40) has, at least in sections, an opening diameter (d40), and the opening diameter of the hollow chamber (d40) is larger than the inner diameter (d20) of the distal transition zone (20). This difference in diameter (d20, d40) has the effect that the liquid (17) is preferably discharged through the aforementioned lateral openings (411, 412, 421, 422) to the surrounding tissue without being able to exit distally (102) through a distal opening (15). Preferably, the distal opening (15) has a smaller diameter (d15) than the inner diameter of the hollow chamber (d40), whereby it is advantageous that the diameter of the distal opening (d15) is approximately equal to the inner diameter of the distal transition zone (20), which is present at least in sections. This means that an inserted guide wire is not subjected to any further diameter changes at the distal opening (15).

As already mentioned, the hollow chamber (40) is directly adjacent to at least one transition zone (20, 30). The transition zone has, at least in sections, a smaller opening diameter (d20, d30) than the hollow chamber (d40). Due to the reduced opening diameter (d20, d30), the dynamic pressure of a liquid (17) forced through is increased in the region of the transition zone (20, 30). This creates an overcoming point for the liquid (17), which would be equivalent to a partially permeable barrier. This could be measured, e.g. via the flow resistance. The flow resistance can be influenced by a pressure difference in the liquid (17), the internal friction, the viscosity and the volume flow of the liquid (17). Structurally, the flow resistance can be influenced by the surface friction, a surface roughness, the diameter and the length of the section to be overcome.

The object of a transition zone (20, 30) according to the invention is, as soon as the liquid (17) is in the hollow chamber (40), to ensure that the liquid (17) preferably flows out through the lateral openings (41, 42) and that the risk of the liquid (17) unintentionally passing through the transition zones (20, 30) is minimised. Therefore, it is the object of the transition zone (20, 30) to provide a section which, compared to the hollow chamber (40), creates a high flow resistance in sections within the transition zone (20, 30). Preferably, the effect of the flow resistance should be direction-dependent (21, 22) on the direction of flow of the liquid (17).

In a preferred embodiment, at least one transition zone (20 and/or 30) exerts a flow resistance, or creates a pressure difference, or influences the internal friction of the liquid (17), or creates a higher surface friction, or influences the volume flow; the difference(s) being higher in a blocking direction (22) than in a forward direction (21). This construction results in a kind of fluidic diode, which is shown with a diode symbol in the following figures (FIG. 3*a*). It is thus possible to distinguish between a forward direction (21) and a blocking direction (22). Whereby it is important to mention that in blocking direction (22) the liquid flow cannot be stopped 100%, because centrally in the transition zone (20, 30) there is always an opening (d20, d30). Rather, with a transition zone, the risk of unintentional leakage can be reduced or not completely eliminated.

In FIG. 3*a* it can be seen that the hollow chamber (40) is distally adjacent to a transition zone (20) and proximally adjacent to a transition zone (30) when viewed from a central plane (106) and the distal transition zone (20) has a forward direction (21) in proximal direction (101) and the proximal transition zone (30) has a forward direction (21) in distal direction (102). It can also be seen that the hollow chamber (40), when viewed from a central plane (106), is distally adjacent to a transition zone (20) and proximally adjacent to a transition zone (30) and the distal transition zone (20) has a blocking direction (22) in distal direction (101) and the proximal transition zone (30) has a blocking direction (22) in proximal direction (102).

The interaction of the two fluidic diodes (20, 30) is illustrated in FIGS. 3*b*, 4*a* and 4*b*. FIG. 3*b* shows a simplified model of the bone anchor. The hollow chamber (40) is shown as a container, which is adjacent to the two fluidic diodes (20 and 30) arranged in opposite directions in their forward direction. An inlet is provided (16) through which a cannula can inject a liquid (17). The hollow chamber (40) has at least one outlet, which is simplified by the lateral openings (41, 42, 411, 412, 421, 422). For completeness, the distal opening (15) is shown simplified as a drain. From the diagram FIG. 4*a* it can be seen how the fluid flow is formed as soon as a liquid (17) is injected through the feed line (16). The proximal fluidic diode (30) is in forward direction and allows the liquid (17) to pass into the hollow chamber (40). The distal fluidic diode (20) is in blocking direction and prevents the liquid from leaking in distal direction (102). The liquid can discharge through the lateral openings (41, 42 etc.).

If the injection cannula is removed, the scenario is different (FIG. 4*b*). The input flow via the opening (16) is interrupted. Only the liquid remains in the hollow chamber (40). The surrounding bone tissue maintains a hydrostatic pressure in the hollow chamber (40). Both fluidic diodes (20, 30) are now active in blocking direction and reduce fluid leakage along the central axis (103). The liquid (17) can only escape through the side openings (41, 42 etc.).

In summary, the proximal transition zone (30) prevents or reduces cement leakage proximally (101). Once the user removes the injection cannula, the hollow chamber (40) will be prevented from depressurising via the proximal access (16). The distal transition zone (20) prevents cement leakage distally (102) to prevent bone cement leakage into the surrounding tissue.

The simplest fluidic diode structure can be created using radially inwardly directed surface elements (24, 34). The transition zone (20, 30) consists of at least one segment (29) having at least one surface element (25, 35, 272, 273) defining the inner opening diameter (d20, d30) and at least one surface element (26, 36) defining a stagnation space, and at least one surface element (24, 34) generating a dynamic pressure in blocking direction (22), wherein the surface element (24, 34) is arranged at an angle to an orthogonal of the central axis (103) between −20° and 20°. The blocking surface elements (24, 34) create a resistance which leads to a local increase of the dynamic pressure, thus generating a back pressure in the liquid (17) and making it more difficult for the liquid to pass through the transition zone (20, 30). The blocking surface elements can be planar (FIG. 5*a, b*), or concave (FIG. 6*a, b*), or convexly curved, or have polygonal elements. It is advantageous if such an arrangement of surface elements and their configurations are repeated segmentally (29) along the central axis (103). This creates an amplification effect of the blocking direction (22). For the sake of completeness, surface elements (23, 33) should also be mentioned, which promote a forward direction (21) of a liquid (17). They do not provide an increased dynamic pressure compared to the blocking direction (22). The surface elements (e.g. 23, 24, 25, 26) are preferably provided as rotary projections rotating around the central axis (103) in the circumferential direction (105). Alternatively, the surface elements can also be protruded in a helix along the central axis (103). In this way, the surface elements can also be produced by classical turning or milling.

In an alternative embodiment, fluidic diodes (20, 30) are provided which exert a dynamic influence on the flow of the liquid (17) and are thus more effective. Optimally, the blocking surface elements (24, 34) have at least a concave curvature (FIG. 7*a, b* and FIG. 8). In order to prevent the liquid from accumulating and remaining there, it is advantageous if a continuous flow of liquid is generated which permanently increases the dynamic pressure and counteracts or changes the main flow of the liquid. This can be achieved by the transition zone (20, 30) consisting of at least one segment (29) having at least one surface element (26, 36) defining a stagnation space, and a ring (27) arranged in said stagnation space. The ring (27) is located within a concentric recess (26, 36) and is supported by support elements (273, 373) in communication with the outer wall (13) of the bone anchor (11). Between the support elements, outer wall and ring, there are spaces which serve to divert the flow of fluid.

The ring (27, 37) defines the opening diameter of the transition zone (d20, d30) with its inner side (272, 273). Optimally, the ring (27, 37) is convexly curved on its radial outside (271, 371). The convex curvature provides a Coanda effect in the liquid so that the liquid is not dammed up but diverted into the main flow.

BRIEF DESCRIPTION OF THE DRAWINGS

FIG. 7*a* illustrates an alternative embodiment of a fluidic diode in forward direction, whereas FIG. 7*b* illustrates the reverse flow principle.

Figure 1:
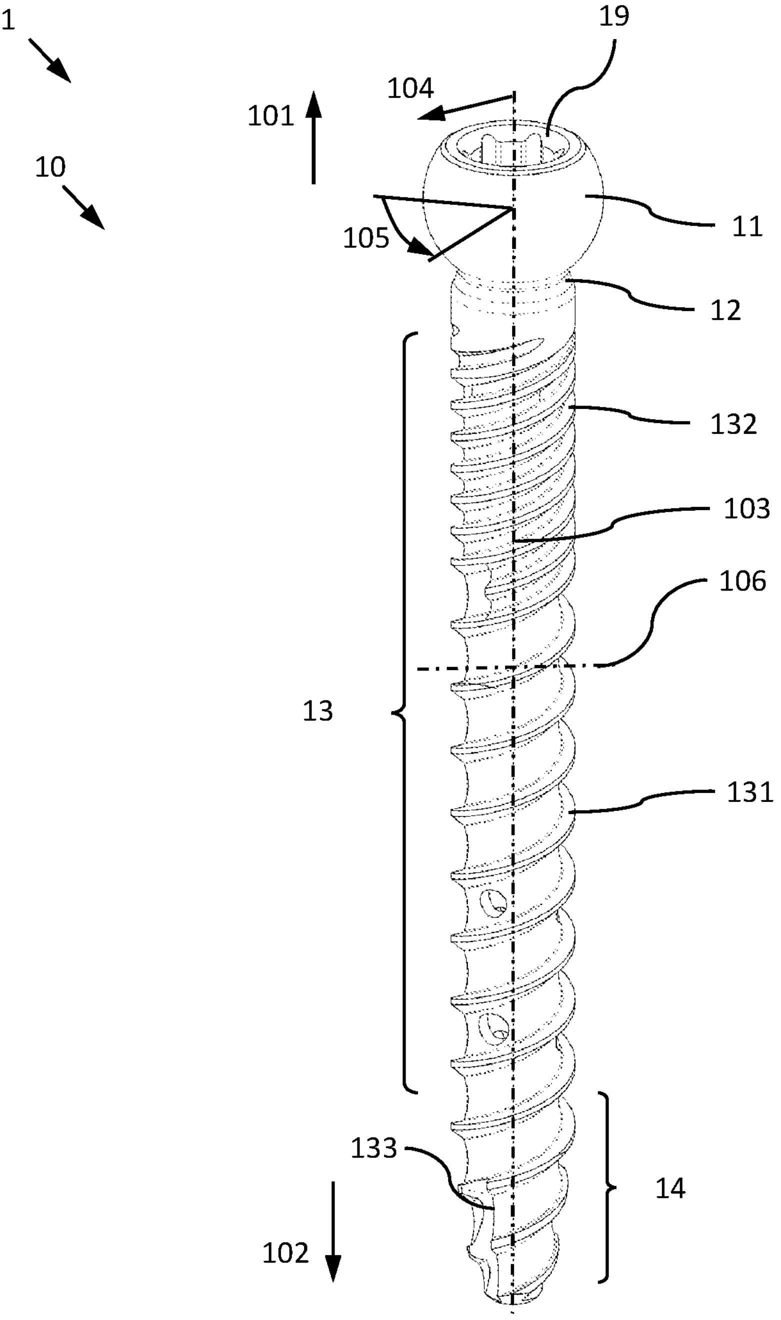
FIG. 1 an oblique view of the bone anchor according to the invention.
Figure 2:
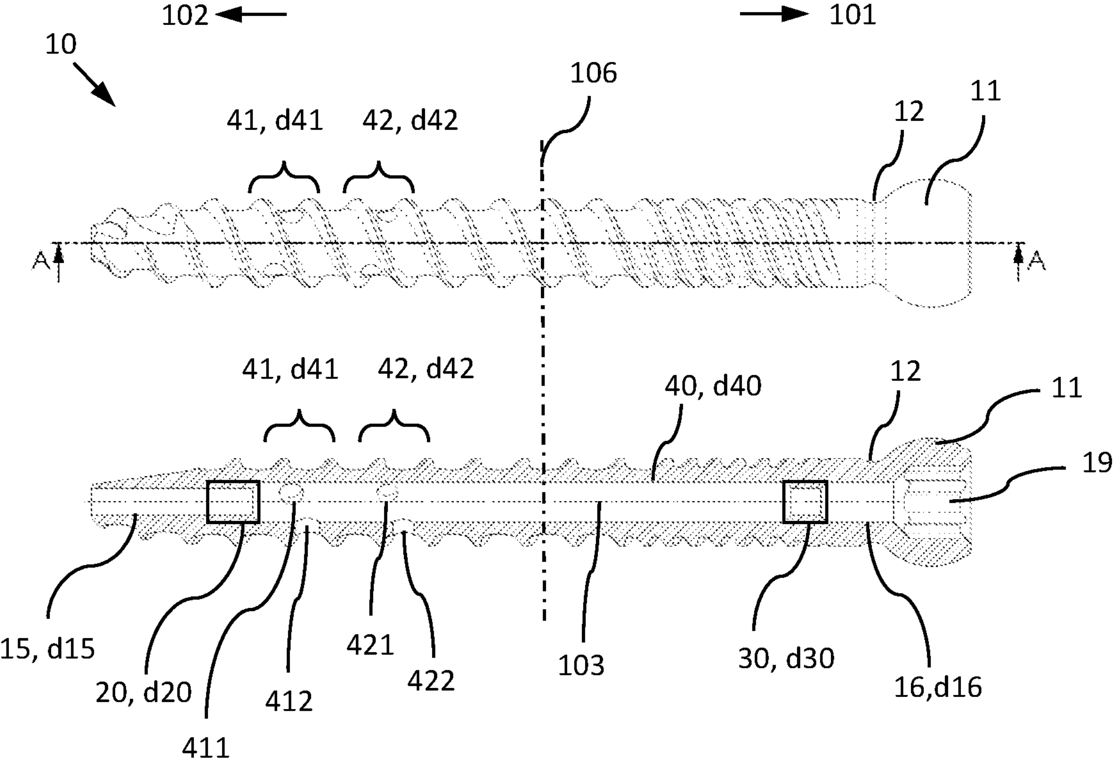
FIG. 2 side view and corresponding sectional view through the bone anchor according to the invention, FIG. 3*a* further sectional view, showing a simplified representation of a fluidic diode, FIG. 3*b* abstract representation of the components relevant to fluid flow, FIG. 4*a* in application of a liquid through a cannula, and FIG. 4*b* immediately after the cannula has been removed.
Figure 3A:
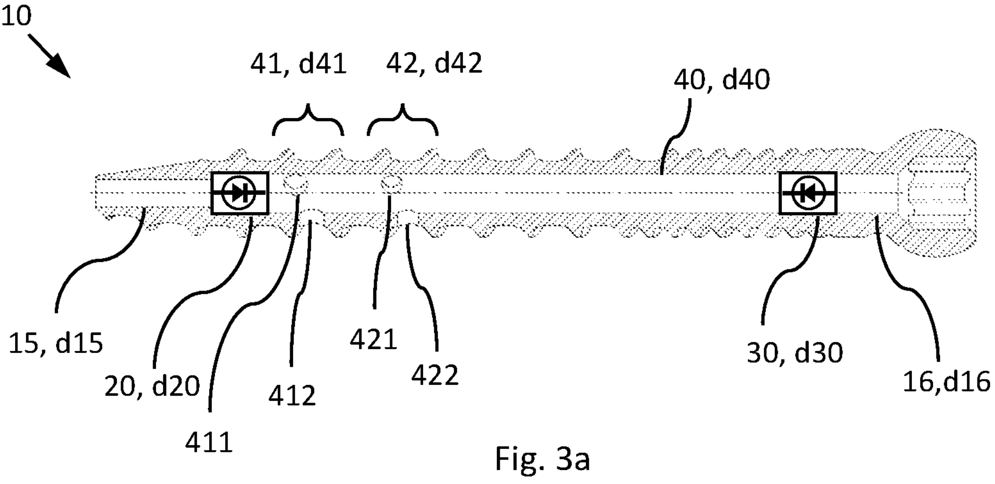
Figure 3B:
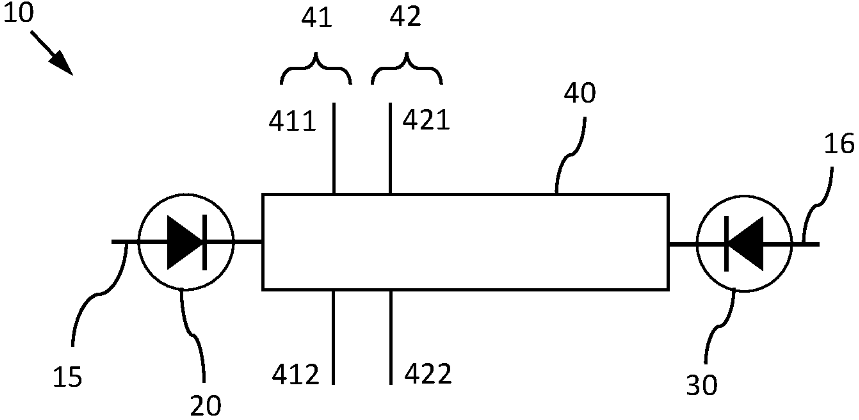
Figure 4A:
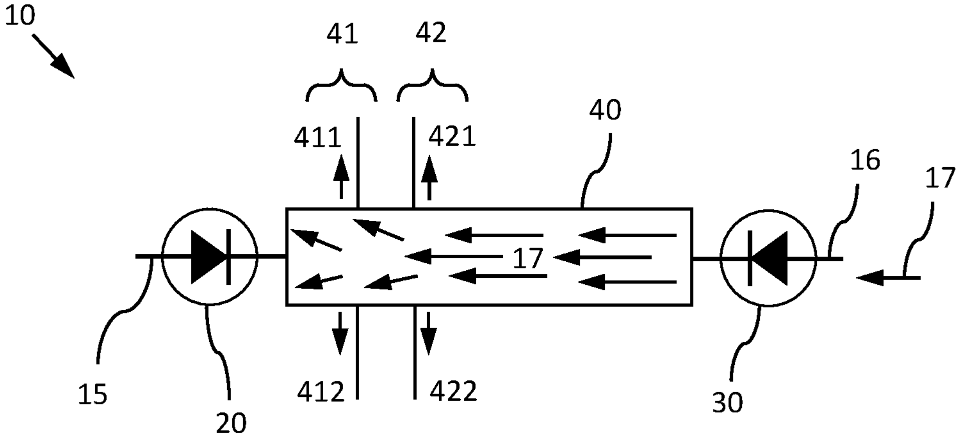
Figure 4B:
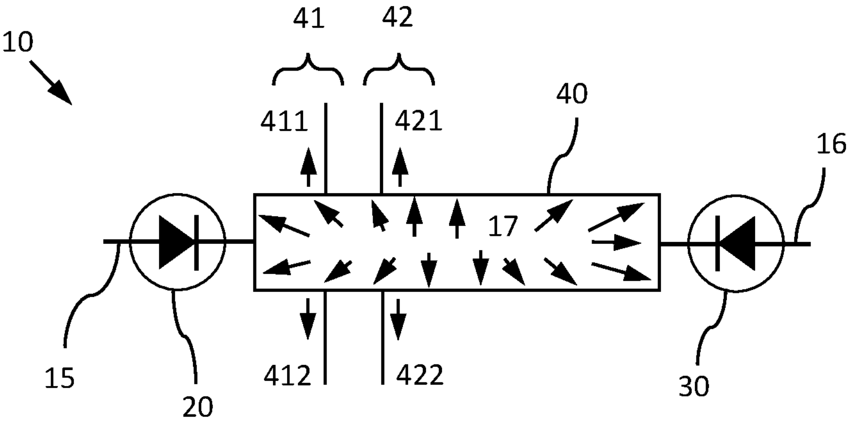
Figures 5A, 5B:
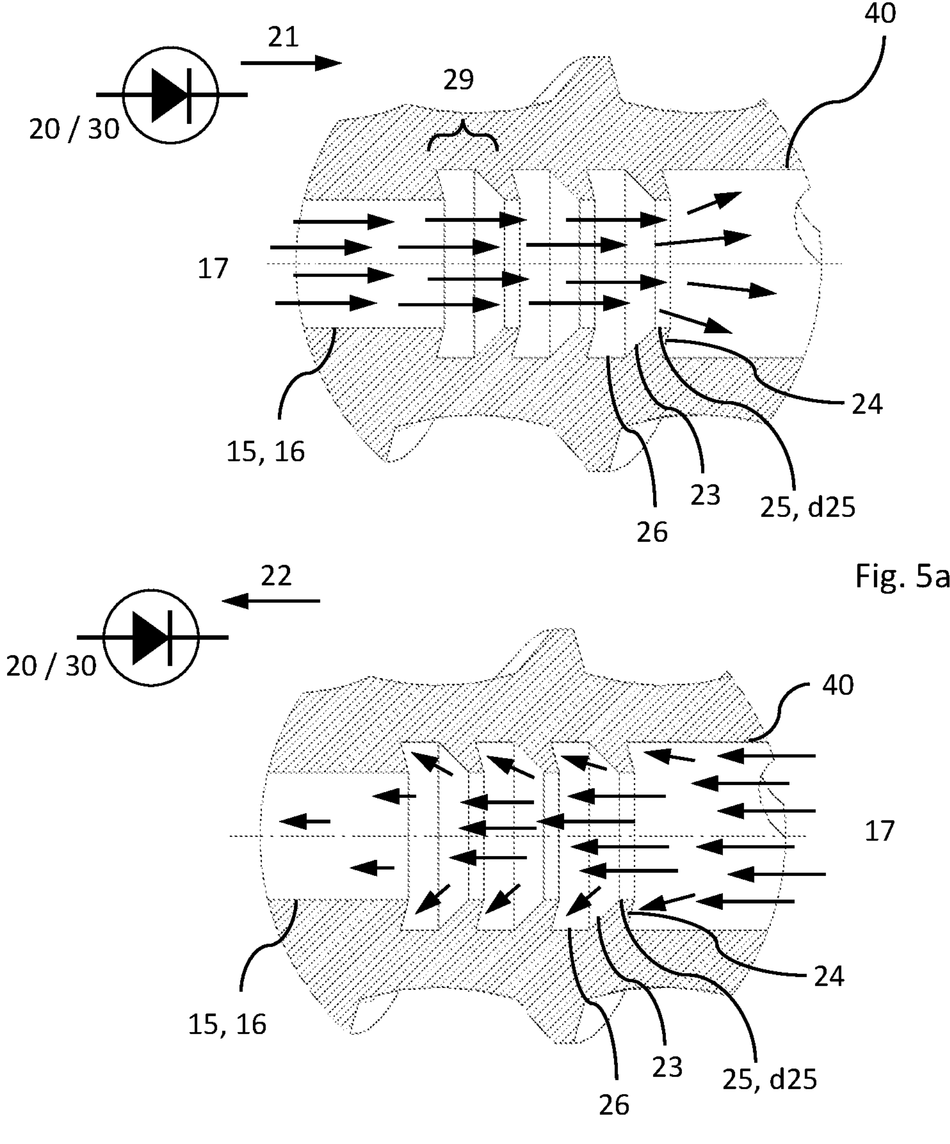
FIG. 5*a* shows a simple form of fluidic diode in the forward direction, and FIG. 5*b* in the blocking direction.
Figure 6A:
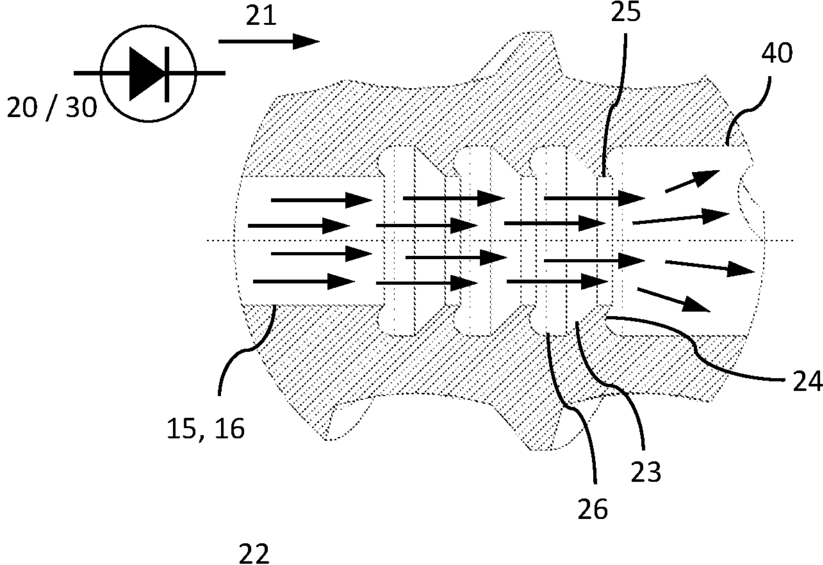
FIG. 6*a* shows the structure of an alternative form of fluidic diode in the forward direction, and FIG. 6*b* in the blocking direction.
Figure 6B:
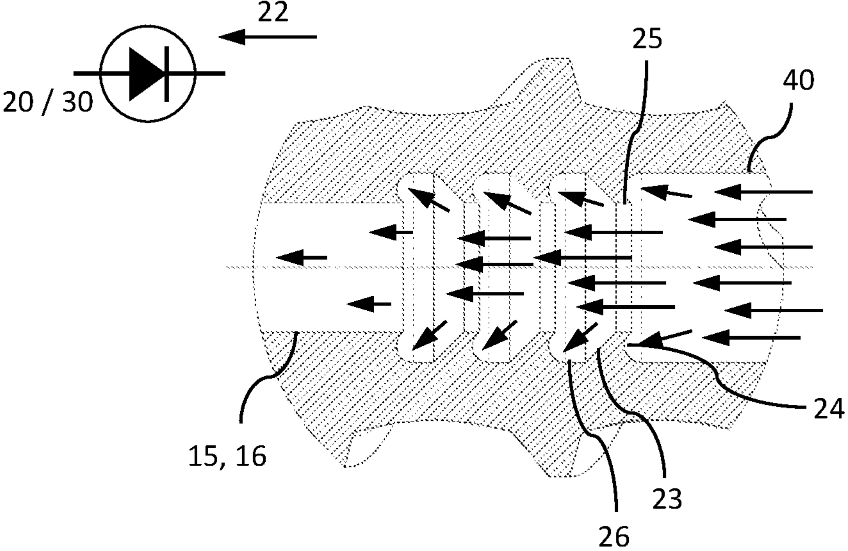
Figures 7A, 7B:
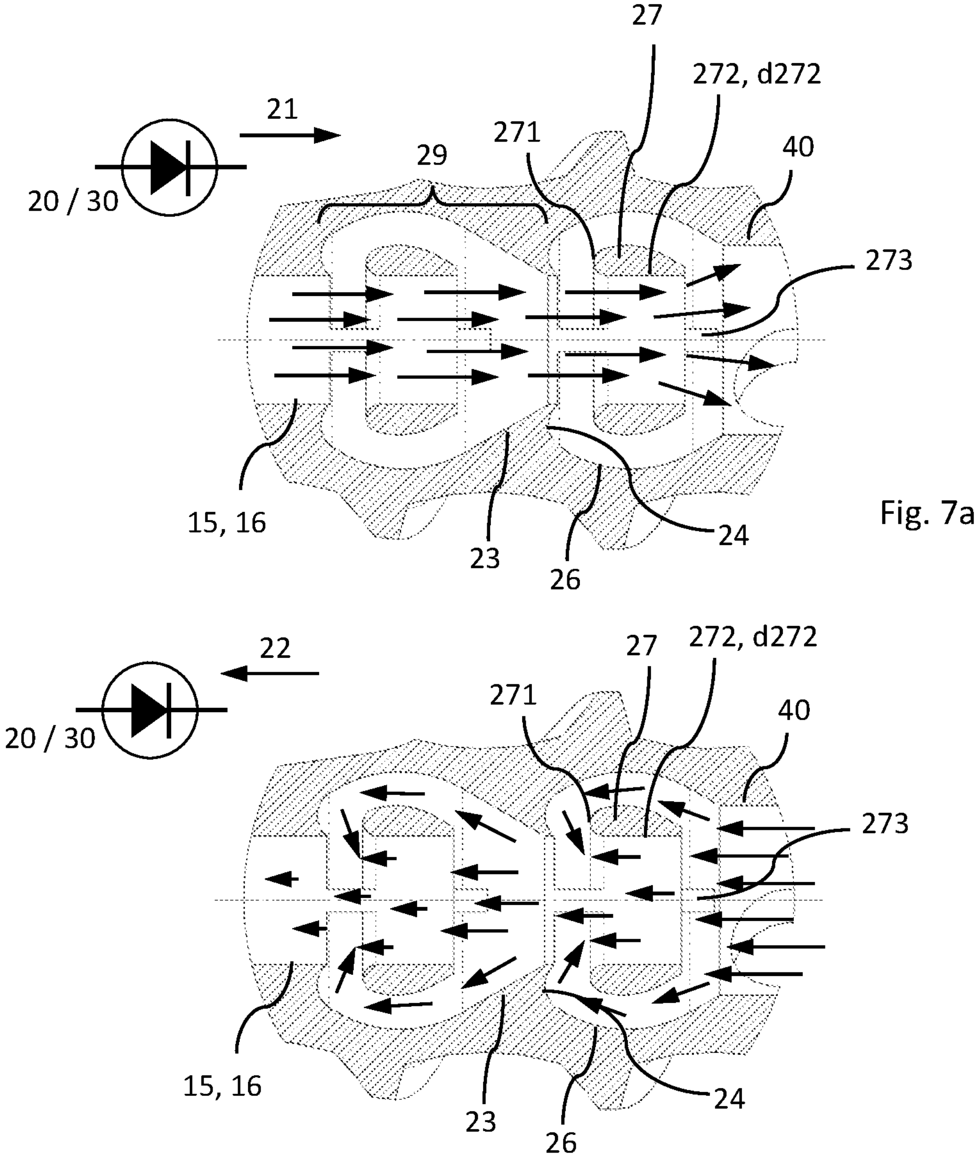
Figure 8:
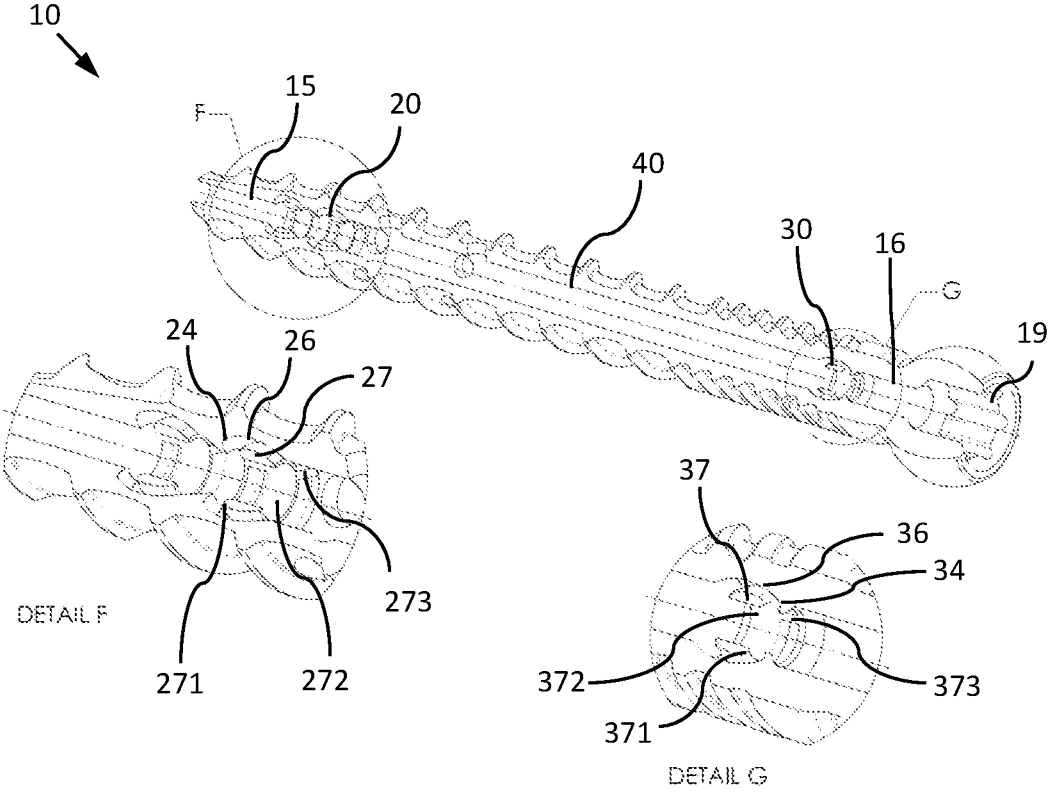
FIG. 8 shows a ¾ section in an oblique view from FIG. 7*a/b*.

The invention claimed is:

1. A bone anchor for the fixation of bone components and bone fragments, comprising a shaft, a neck area and a head located in a proximal direction and a tip located in a distal direction; wherein the bone anchor has a mainly cylindrically shaped hollow chamber extending along a central axis; wherein the hollow chamber is adjacent a proximal transition zone located proximally from a central plane perpendicular to the central axis; wherein the proximal transition zone has an inner diameter and the hollow chamber has an opening diameter; and the opening diameter of the hollow chamber is greater than the inner diameter of the proximal transition zone; wherein the proximal transition zone defines a section which causes a higher flow resistance compared to a section of the same length of the hollow chamber; said section of the proximal transition zone having a ring, wherein an inner surface of the ring defines the inner diameter, the ring is held in said section of the proximal transition zone by support elements in communication with an outer wall of the bone anchor, wherein the ring is located within a concentric radial recess defining a stagnation space with an outer diameter greater than the inner diameter so that the radial recess is formed in a side of said section of the proximal transition zone, and spaces between the support elements, the outer wall, and an outer surface of the ring are configured to divert a flow of fluid therethrough, and said section of the proximal transition zone further comprises a blocking surface element which is located proximal to the stagnation space and is configured to generate a dynamic pressure in a blocking direction.

2. The bone anchor according to claim 1, wherein in further proximal course along the central axis an opening adjoins the proximal transition zone, which is suitable for receiving a cannula at least in sections.

3. The bone anchor according to claim 1, wherein an opening diameter of an opening proximally adjacent to the proximal transition zone is greater than at least one portion of the inner diameter of the proximal transition zone.

4. The bone anchor according to claim 1, wherein an opening opens in the proximal direction into a tool attachment point.

5. The bone anchor according to claim 1, wherein the hollow chamber adjoins a distal transition zone located distally from the central plane, and the distal transition zone has an inner diameter, and the opening diameter of the hollow chamber is greater than the inner diameter of the distal transition zone.

6. The bone anchor according to claim 1, wherein the section of the proximal transition zone causes a higher pressure in a liquid compared to the section of the same length in the hollow chamber.

7. The bone anchor according to claim 1, wherein the section of the proximal transition zone leads to a higher internal friction in a liquid compared to the section of the same length of the hollow chamber.

8. The bone anchor according to claim 1, wherein the proximal transition zone has a higher surface friction coefficient or a higher surface roughness than the hollow chamber.

9. The bone anchor according to claim 1, wherein the proximal transition zone allows a smaller volume flow of liquid than the hollow chamber.

10. The bone anchor according to claim 1, wherein the ring is convexly curved at a radial outside.

11. The bone anchor according to claim 1, wherein the proximal transition zone causes a difference in at least one of a flow resistance, or pressure, or internal friction of a liquid, or volume flow, and said difference is dependent on a flow direction of the liquid.

12. The bone anchor according to claim 1, wherein the proximal transition zone has a blocking direction and a forward direction for liquids.

13. The bone anchor according to claim 1, wherein the hollow chamber, as viewed from the central plane, is distally adjacent to a distal transition zone and proximally adjacent to the proximal transition zone, and the distal transition zone has a forward direction in the proximal direction and the proximal transition zone has a forward direction in the distal direction.

14. The bone anchor according to claim 1, wherein the hollow chamber, as viewed from the central plane, is distally adjacent to a distal transition zone and proximally adjacent to the proximal transition zone, and the distal transition zone has a blocking direction in the distal direction and the proximal transition zone has a blocking direction in the proximal direction.

15. The bone anchor according to claim 1, wherein the hollow chamber has at least one laterally extending opening communicating with the hollow chamber.

16. The bone anchor according to claim 1, wherein the bone anchor is formed in one piece.

17. The bone anchor according to claim 1, further comprising an opening extending throughout the bone anchor along the central axis.

* * * * *